United States Patent [19] [11] 4,163,057
Nadelson [45] Jul. 31, 1979

[54] ISOXAZOLE-4-CARBOXAMIDES AS TRANQUILIZERS, SLEEP-INDUCERS AND MUSCLE RELAXANTS

[75] Inventor: Jeffrey Nadelson, Denville, N.J.
[73] Assignee: Sandoz, Inc., East Hanover, N.J.
[21] Appl. No.: 864,380
[22] Filed: Dec. 27, 1977
[51] Int. Cl.² .................. A61K 31/42; C07D 261/14; C07D 261/10
[52] U.S. Cl. .................. 424/272; 260/307 H; 260/326.43; 568/584; 260/645; 260/646
[58] Field of Search .................. 260/307 H; 424/272
[56] References Cited
U.S. PATENT DOCUMENTS
3,498,995   3/1970   McGregor et al. .................. 260/302

Primary Examiner—Raymond V. Rush
Attorney, Agent, or Firm—Gerald D. Sharkin; Robert S. Honor; Timothy G. Rothwell

[57] ABSTRACT

Compounds of the formula

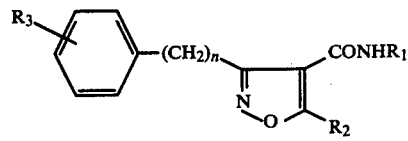

where
$R_1$ is hydrogen or lower alkyl, and
$R_2$ is hydrogen or straight chain lower alkyl, and
$R_3$ is hydrogen, fluoro, chloro, lower alkoxy, lower alkyl or trifluoromethyl, and
n is 1, 2, 3, and 4, which are useful as minor tranquilizers, sleep inducers and muscle relaxants.

9 Claims, No Drawings

ISOXAZOLE-4-CARBOXAMIDES AS TRANQUILIZERS, SLEEP-INDUCERS AND MUSCLE RELAXANTS

This invention relates to substituted isoxazole-4-carboxamides which exhibit minor tranquilizer, sleep inducer and muscle relaxant activity. In particular, it relates to unsubstituted isoxazole-4-carboxamides, and intermediates thereof.

The compounds of this invention may be represented by the following structural formula:

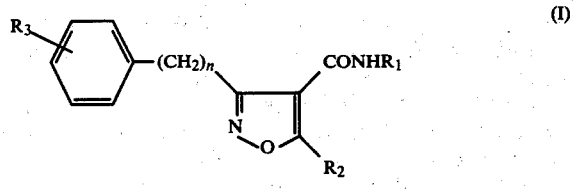

where
$R_1$ is hydrogen or lower alkyl, i.e., alkyl having 1 to 4 carbon atoms, e.g., methyl, ethyl, isopropyl and the like, and
$R_2$ is hydrogen or straight chain lower alkyl, i.e., straight chain lower alkyl having 1 to 4 carbon atoms, e.g., methyl, ethyl, propyl and the like, and
$R_3$ is hydrogen, fluoro, chloro, lower alkoxy, i.e., alkoxy having 1 to 4 carbon atoms, e.g., methoxy, ethoxy, isopropoxy and the like, lower alkyl, i.e., alkyl having 1 to 4 carbon atoms, e.g., methyl, ethyl, isopropyl and the like, or trifluoromethyl, and
n is 1, 2, 3, or 4.

The compounds of formula (I) are prepared according to the following reaction scheme:

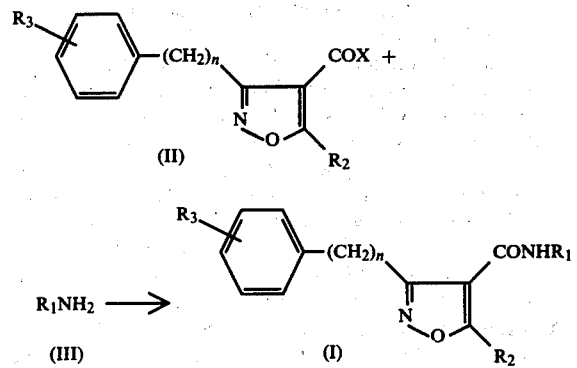

where
X is chlorine or bromine, and
$R_1$, $R_2$, $R_3$ and n are as defined above.

The compounds of formula (I) are prepared by reacting a compound of the formula (II) with a compound of the formula (III) in the presence of an inert organic solvent. Although the particular solvent employed is not critical the preferred solvents include the aromatic hydrocarbons such as benzene, toluene and the like, the halogenated hydrocarbons such as methylene dichloride, chloroform and the like or the ethers, such as tetrahydrofuran or diethylether, the latter being especially preferred. The temperature of the reaction is not critical, but it is preferred that the reaction be carried out at a temperature between about 0° to 50° C., preferably from about 20° to 35° C. The reaction may be run from 2 to 24 hours, preferably from about 10 to 16 hours. The product is recovered using conventional techniques, e.g., filtration.

The compounds of formula (II) are prepared in accordance with the following reaction scheme:

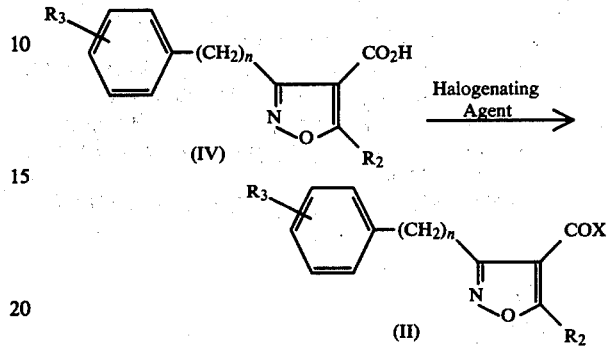

where X, $R_2$, $R_3$ and n are as defined above.

The compounds of formula (II) are prepared by reacting a compound of the formula (IV) with a halogenating agent optionally in the presence of an inert organic solvent. The preferred halogenating agents include thionyl chloride, thionyl bromide, phosphorous oxychloride, phosphorous pentachloride and the like, especially thionyl chloride. Although an inert organic solvent such as an aromatic hydrocarbon, e.g., benzene, toluene, and the like or a halogenated hydrocarbon such as methylene dichloride and the like can be employed, it is preferred that the reaction be carried out in an excess of the halogenating agent employed, e.g., thionyl chloride. The temperature of the reaction is not critical, but it is preferred that the reaction be carried out at a temperature between about 40° to 130° C., preferably the reflux temperature of the solvent. The reaction may be run from 1 to 7 hours, preferably from about 2 to 4 hours. The product is recovered by conventional techniques, e.g., evaporation.

The compounds of formula (IV) are prepared according to the following reaction scheme:

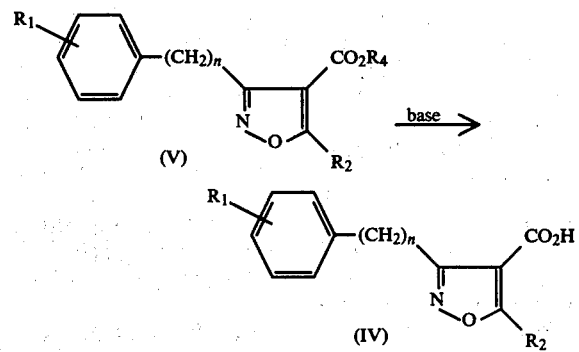

where
$R_4$ is lower alkyl having 1 to 2 carbon atoms, and
$R_2$, $R_3$ and n are as defined above.

The compounds of formula (IV) are prepared by reacting a compound of the formula (V) with a strong inorganic base in the presence of an aqueous solvent. Although the particular inorganic base employed is not critical, the preferred bases include the alkali metal hydroxides, for example potassium hydroxide, sodium hydroxide, lithium hydroxide and the like, especially potassium hydroxide. The particular aqueous solvent employed is not critical, but it is preferred that the reaction be run in water, or any inert water miscible solvent including the lower alkanols, e.g., methanol, ethanol, and the like, acetone or dioxane, preferably ethanol. The temperature of the reaction is not critical, but it is preferred that the reaction be run at a temperature of from about 25° to 125° C., preferably from about 40° to 80° C. The reaction is run from about 1 to 24 hours, preferably from about 4 to 16 hours. The product is recovered using conventional techniques, e.g., filtration followed by trituration.

The compounds of formula (V) are prepared according to the following reaction scheme:

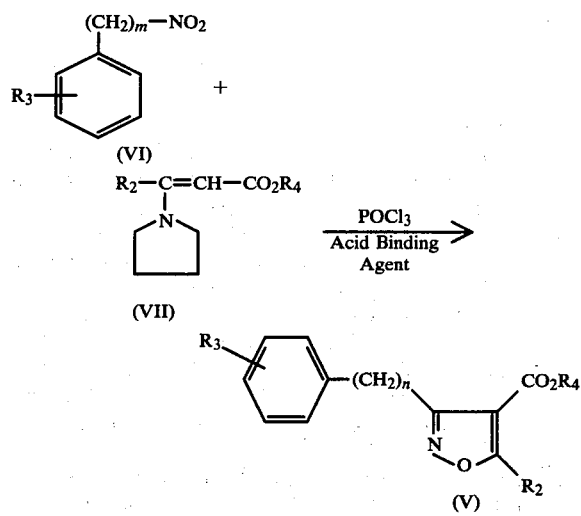

where
m is 2, 3, 4 or 5, and
$R_2$, $R_3$, $R_4$ and n are as defined above.

The compounds of formula (V) are prepared by reacting a compound of the formula (VI) with a compound of the formula (VII) in the presence of phosphorous oxychloride, an acid binding agent such as pyridine, diisopropylethylamine or triethylamine, the latter being especially preferred, and an inert organic solvent. Although the particular solvent employed is not critical, it is preferred that the reaction be carried out in the presence of the halogenated hydrocarbons such as methylene-dichloride, chloroform, carbon tetrachloride and the like, preferably chloroform. The temperature of the reaction is not critical, but it is preferred that the reaction be run from about −10° to about +30° C., preferably from about 5° to 20° C. The reaction is run from about 3 to 20 hours, preferably from about 14 to 18 hours. The product is recovered using conventional techniques, e.g., distillation.

Many of the compounds of formulae (III), (VI), and (VII) are known and may be prepared by methods described in the literature for example *Arkiv Kemi*, Vol. 24, 519–530 (1965), and *Tetrahedron Letters*, No. 1, 71–74 (1975). The compounds of formulae (III), (VI), and (VII) not specifically described may be prepared by analogous methods from known starting materials.

The compounds of formula (I) are useful because they possess pharmacological activity in animals as sleep inducers, minor tranquilizers and muscle relaxants as indicated (1) by the hexobarbital reinduction method of Winter, J. Pharmacol. and Exp. Therap. 94, 7–11, 1948, in which the reinduction of anethesia is used to determine sedative-hypnotic activity in mice given 70 mg/kg. of animal body weight i.p. of hexobarbital followed immediately after the mice regain their righting reflexes by 40.00 to 100 mg/kg. of animal body weight i.p. of the test compound; (2) by their ability to produce docility in behavior tests in mice given 75.0 to 200 mg/kg. of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chronic convulsions and death in mice given about 75.0 to 200 mg/kg. of the test compound followed immediately by 50 mg/kg. i.p. of N-sulfamoylazepine; (4) by scoring for loss of righting reflex according to the method of Reed-Muench (American Journal of Hygiene, 27: 493–497), in which mice are administered 12.5 mg/kg. i.p. Thioridazine, immediately after which the test compound is administered at dosages of 100 to 200 mg/kg. in a volume of 0.1 ml/10 g. body weight. Sixty minutes after dosing, the mice are scored for loss of righting reflex; and (5) by the rotarod test as described by Dunham and Miya (J. Am. Pharm. Assoc., 45: 208, 1957).

For such usage, the compounds (I) may be combined with a pharmaceutically acceptable carrier or adjuvant and may be administered orally or parenterally as such or admixed with conventional pharmacetuical carriers. They may be administered in such forms as tablets, dispersible powders, granules, capsules, syrups and elixirs and parenterally as solutions, suspensions, dispersions, emulsions, and the like, e.g., a sterile injectable aqueous solution. The dosage will vary depending upon the mode of administration utilized and the particular compound employed.

The sleep inducing effective dosage of the compounds of formula (I) will vary depending on the particular compound employed. However, in general, satisfactory results are obtained when the compounds are administered orally at a daily dosage of from about 10.0 milligrams to about 200 milligrams per kilogram of animal body weight, typically given in a single dose at bedtime. For most large mammals, the total daily dosage is from about 150 to about 1500 milligrams, preferably at bedtime and dosage forms suitable for internal administration comprise from about 37.5 to about 750 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use in the treatment of anxiety and tension, the effective dosage will vary depending on the particular compound employed. However, in general, satisfactory results are obtained when the compounds are administered orally at a daily dosage of from about 1.0 milligrams to about 100 milligrams per kilogram of animal body weight, typically given in divided doses two to four times per day. For most large mammals, the total daily dosage is from about 75.0 to about 750 milligrams, and dosage forms suitable for internal administratIon comprise from about 17.5 to about 375 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compounds are administered orally at a daily dosage of from about 25 milligrams to about 500 milligrams per kilogram of animal body weight typically given in divided doses two to four times per day. For most large mammals, the total daily dosage is from about 200 to about 2500 milligrams and dosage forms suitable for internal administration comprise from about 50 to about 1000 milligrams of the compound in admixture with a solid or liquid pharmaceutical carrier or diluent.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers and muscle relaxants in divided doses two to four times per day.

| INGREDIENTS | WEIGHT (mg) Tablet | Capsule |
|---|---|---|
| 3-phenethyl-5-methyl-isoxazole-4-carboxamide | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

3-Phenethyl-5-methyl-isoxazole-4-carboxylic acid ethyl ester

A mixture of 48.5 g. (0.265 mole) ethyl-3-pyrrolidone crotonate 48.2 g. (0.291 mole) 1-nitro-3-phenylpropane and 208 ml. (1.490 mole) triethylamine in 500 ml. chloroform is cooled to 0° and treated by the dropwise addition of 44.6 g. (0.291 mole) phosphorous oxychloride in 105 ml. chloroform. The addition takes approximately three hours and the temperature is maintained at about 0°±5°. After the addition the mixture is stirred at room temperature over night. The resulting mixture is then washed once with cold water, three times with 6 N hydrochloric acid, once with 1 N sodium hydroxide and once with saturated sodium chloride. The organic layer is dried over anhydrous magnesium sulfate, filtered and evaporated in vacuo. The residue is distilled and the fraction collected at about 145°-150°/0.45 mm to give 3-phenethyl-5-methyl-isoxazole-4-carboxylic acid ethyl ester. Identified by NMR and IR.

Following the above procedure and using in place of 1-nitro-3-phenylpropane an equivalent amount of
(a) 1-nitro-2-phenylethane,
(b) 1-nitro-4-phenylbutane, or
(c) 1-nitro-5-phenylpentane there is obtained
(a) 3-benzyl-5-methyl-isoxazole-4-carboxylic acid ethyl ester,
(b) 3-(3-phenylpropyl)-5-methyl-isoxazole-4-carboxylic acid ethyl ester, or
(c) 3-(4-phenylbutyl)-5-methyl-isoxazole-4-carboxylic acid ethyl ester, respectively.

Also following the above procedure and using in place of 1-nitro-3-phenylpropane an equivalent amount of
(d) 1-nitro-3-(4-fluorophenyl)-propane
(e) 1-nitro-3-(4-chlorophenyl)-propane,
(f) 1-nitro-3-(4-tolyl)-propane,
(g) 1-nitro-3-(4-methoxyphenyl)-propane, or
(h) 1-nitro-3-(3-trifluoromethylphenyl)-propane there is obtained
(d) 3-(4-fluorophenethyl)-5-methyl-isoxazole-4-carboxylic acid ethyl ester,
(e) 3-(4-chlorophenethyl)-5-methyl-isoxazole-4-carboxylic acid ethyl ester,
(f) 3-(4-methylphenethyl)-5-methyl-isoxazole-4-carboxylic acid ethyl ester,
(g) 3-(4-methoxyphenethyl)-5-methyl-isoxazole-4-carboxylic acid ethyl ester, or
(h) 3-(3-trifluoromethylphenethyl)-5-methyl-isoxazole-4-carboxylic acid ethyl ester, respectively.

Also following the above procedure and using in place of ethyl-3-pyrrolidone crotonate an equivalent amount of ethyl-3-pyrrolidone acrylate there is obtained
(i) 3-phenethyl-isoxazole-4-carboxylic acid ethyl ester.

EXAMPLE 2

3-Phenethyl-5-methyl-isoxazole-4-carboxylic acid

A mixture of 300 g. (1.30 mole) 3-phenethyl-5-methyl-isoxazole-4-carboxylic acid ethyl ester, 146 g. (1.60 mole) potassium hydroxide 1500 ml. ethanol and 500 ml. water is stirred for 2 hours at room temperature and 2 additional hours at reflux. The ethanol is evaporated in vacuo and the aqueous solution is cooled and acidified with hydrochloric acid. The resulting solid is filtered and washed with water and triturated with methanol to give 3-phenethyl-5-methyl-isoxazole-4-carboxylic acid; m.p. 154° to 156° C.

Following the above procedure and using in place of 3-phenethyl-5-methyl-isoxazole-4-carboxylic acid ethyl ester an equivalent amount of
(a) 3-benzyl-5-methyl-isoxazole-4-carboxylic acid ethyl ester,
(b) 3-(3-phenylpropyl)-5-methyl-isoxazole-4-carboxylic acid ethyl ester,
(c) 3-(4-phenylbutyl)-5-methyl-isoxazole-4-carboxylic acid ethyl ester,
(d) 3-(4-fluorophenethyl)-5-methyl-isoxazole-4-carboxylic acid ethyl ester,
(e) 3-(4-chlorophenethyl)-5-methyl-isoxazole-4-carboxylic acid ethyl ester,
(f) 3-(4-methylphenethyl)-5-methyl-isoxazole-4-carboxylic acid ethyl ester,
(g) 3-(4-methoxyphenethyl)-5-methyl-isoxazole-4-carboxylic acid ethyl ester,
(h) 3-(3-trifluoromethylphenethyl)-5-methyl-isoxazole-4-carboxylic acid ethyl ester, or
(i) 3-phenethyl-isoxazole-4-carboxylic acid ethyl ester
there is obtained
(a) 3-benzyl-5-methyl-isoxazole-4-carboxylic acid,
(b) 3-(3-phenylpropyl)-5-methyl-isoxazole-4-carboxylic acid,
(c) 3-(4-phenylbutyl)-5-methyl-isoxazole-4-carboxylic acid,
(d) 3-(4-fluorophenethyl)-5-methyl-isoxazole-4-carboxylic acid, (e) 3-(4-chlorophenethyl)-5-methyl-isoxazole-4-carboxylic acid,
(f) 3-(4-methylphenethyl)-5-methyl-isoxazole-4-carboxylic acid,
(g) 3-(4-methoxyphenethyl)-5-methyl-isoxazole-4-carboxylic acid,
(h) 3-(3-trifluoromethylphenethyl)-5-methyl-isoxazole-4-carboxylic acid, or
(i) 3-phenethyl-isoxazole-4-carboxylic acid, respectively.

EXAMPLE 3

3-Phenethyl-5-methyl-isoxazole-4-carboxylic acid chloride

A mixture of 23.1 g. (0.10 mole) 3-phenethyl-5-methyl-isoxazole-4-carboxylic acid and 300 ml. thionyl chloride is heated at reflux for 2½ hours. The resulting mixture is cooled and the excess thionyl chloride removed in vacuo. The residue is dissolved in benzene and the benzene evaporated in vacuo. This is repeated three times to remove last traces of thionyl chloride. The crude 3-phenethyl-5-methyl-isoxazole-4-carboxylic acid chloride is employed in situ without purification in the preparation of the final compounds.

Following the above procedure and using in place of 3-phenethyl-5-methyl-isoxazole-4-carboxylic acid an equivalent amount of (a) 3-benzyl-5-methyl-isoxazole-4-carboxylic acid,
(b) 3-(3-phenylpropyl)-5-methyl-isoxazole-4-carboxylic acid,
(c) 3-(4-phenylbutyl)-5-methyl-isoxazole-4-carboxylic acid,
(d) 3-(4-fluorophenethyl)-5-methyl-isoxazole-4-carboxylic acid,
(e) 3-(4-chlorophenethyl)-5-methyl-isoxazole-4-carboxylic acid,
(f) 3-(4-methylphenethyl)-5-methyl-isoxazole-4-carboxylic acid,
(g) 3-(4-methoxyphenethyl)-5-methyl-isoxazole-4-carboxylic acid,
(h) 3-(3-trifluoromethylphenethyl)-5-methyl-isoxazole-4-carboxylic acid,
(i) 3-phenethyl-isoxazole-4-carboxylic acid there is obtained (a) 3-benzyl-5-methyl-isoxazole-4-carboxylic acid chloride,
(b) 3-(3-phenylpropyl)-5-methyl-isoxazole-4-carboxylic acid chloride,
(c) 3-(4-phenylbutyl)-5-methyl-isoxazole-4-carboxylic acid chloride,
(d) 3-(4-fluorophenethyl)-5-methyl-isoxazole-4-carboxylic acid chloride,
(e) 3-(4-chlorophenethyl)-5-methyl-isoxazole-4-carboxylic acid chloride,
(f) 3-(4-methylphenethyl)-5-methyl-isoxazole-4-carboxylic acid chloride,
(g) 3-(4-methoxyphenethyl)-5-methyl-isoxazole-4-carboxylic acid chloride,
(h) 3-(3-trifluoromethylphenethyl)-5-methyl-isoxazole-4-carboxylic acid chloride, or
(i) 3-phenethyl-isoxazole-4-carboxylic acid chloride, respectively.

EXAMPLE 4

3-Phenethyl-5-methyl-isoxazole-4-carboxamide

A mixture of 24.9 g. (0.10 mole) 3-phenethyl-5-methyl-isoxazole-4-carboxylic acid chloride in 100 ml. diethyl ether is added to 7.7 g. (0.2 mole) of concentrated ammonium hydroxide while maintaining the temperature at 0° to 10° C. The mixture is stirred at room temperature overnight and filtered. The resulting solid is washed with water and dried to give 3-phenethyl-5-methyl-isoxazole-4-carboxamide; m.p. 135° to 136° C.

Following the above procedure and using in place of 3-phenethyl-5-methyl-isoxazole-4-carboxylic acid chloride an equivalent amount of.

(a) 3-benzyl-5-methyl-isoxazole-4-carboxylic acid chloride,
(b) 3-(3-phenylpropyl)-5-methyl-isoxazole-4-carboxylic acid chloride,
(c) 3-(4-phenylbutyl)-5-methyl-isoxazole-4-carboxylic acid chloride,
(d) 3-(4-fluorophenethyl)-5-methyl-isoxazole-4-carboxylic acid chloride,
(e) 3-(4-chlorophenethyl)-5-methyl-isoxazole-4-carboxylic acid chloride,
(f) 3-(4-methylphenethyl)-5-methyl-isoxazole-4-carboxylic acid chloride,
(g) 3-(4-methoxyphenethyl)-5-methyl-isoxazole-4-carboxylic acid chloride,
(h) 3-(3-trifluoromethylphenethyl)-5-methyl-isoxazole-4-carboxylic acid chloride, or
(i) 3-phenethyl-isoxazole-4-carboxylic acid chloride, there is obtained (a) 3-benzyl-5-methyl-isoxazole-4-carboxamide,
(b) 3-(3-phenylpropyl)-5-methyl-isoxazole-4-carboxamide,
(c) 3-(4-phenylbutyl)-5-methyl-isoxazole-4-carboxamide,
(d) 3-(4-fluorophenethyl)-5-methyl-isoxazole-4-carboxamide,
(e) 3-(4-chlorophenethyl)-5-methyl-isoxazole-4-carboxamide,
(f) 3-(4-methylphenethyl)-5-methyl-isoxazole-4-carboxamide,
(g) 3-(4-methoxyphenethyl)-5-methyl-isoxazole-4-carboxamide,
(h) 3-(3-trifluoromethylphenethyl)-5-methyl-isoxazole-4-carboxamide, or
(i) 3-phenethyl-isoxazole-4-carboxamide, respectively.

Again following the above procedure and using in place of ammonium hydroxide an equivalent amount of methylamine there is obtained N-methyl-3-phenethyl-5-methyl-isoxazole-4-carboxamide.

The 3-phenethyl-5-methyl-isoxazole-4-carboxamide of this example is an effective minor tranquilizer when orally administered to an animal in need of said treatment at a dosage of 100 milligrams two to four times per day. The compound of this example is also effective as a sleep inducer when orally administered to an animal in need of said treatment at a dosage of 250 milligrams just before bedtime.

Furthermore, the 3-phenethyl-5-methyl-isoxazole-4-carboxamide of this example is an effective muscle-relaxant when orally administered to an animal in need of said treatment at a dosage of 200 milligrams two to four times per day.

What is claimed is:

1. A compound of the formula

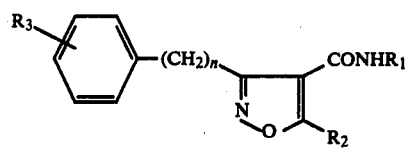

where
 R₁ is hydrogen or lower alkyl having 1 to 4 carbon atoms, and
 R₂ is hydrogen or straight chain lower alkyl having 1 to 4 carbon atoms, and
 R₃ is hydrogen, fluoro, chloro, lower alkoxy having 1 to 4 carbon atoms or trifluoromethyl,
and
 n is 1, 2, 3 or 4.

2. A compound of the formula

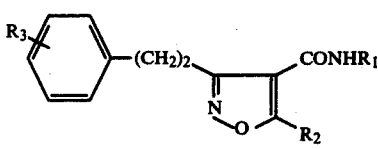

where
 R₁, R₂, and R₃ are as defined above.

3. A compound of the formula

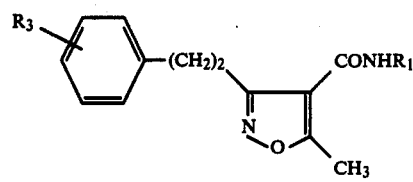

where
 R₁ and R₃ are as defined above.

4. The compound of claim 3 which is 3-phenethyl-5-methyl-isoxazole-4-carboxamide.

5. The compound of claim 3 which is N-methyl-3-phenethyl-5-methyl-isoxazole-4-carboxamide.

6. The method of treating insomnia which comprises administering to a mammal in need of said treatment a sleep inducer effective amount of a compound according to claim 1.

7. The method of treating anxiety, which comprises administering to a mammal in need of said treatment an anti-anxiety effective amount of a compound according to claim 1.

8. The method of treating muscle spasms, which comprises administering to a mammal in need of said treatment a muscle-relaxant effective amount of a compound according to claim 1.

9. A pharmaceutical composition which comprises a pharmacologically effective amount of a compound of claim 1 and a pharmaceutically acceptable diluent or carrier therefor.

* * * * *

UNITED STATES PATENT AND TRADEMARK OFFICE
CERTIFICATE OF CORRECTION

PATENT NO. : 4,163,057
DATED : Jul. 31, 1979
INVENTOR(S) : Jeffrey Nadelson

It is certified that error appears in the above-identified patent and that said Letters Patent are hereby corrected as shown below:

Col. 9, line 30, after the word "defined", please delete the word "above" and insert in its place -- in claim 1 --.

Col. 10, line 11, after the word "defined", please delete the word "above" and insert in its place -- in claim 1 --.

Signed and Sealed this

Twenty-second Day of January 1980

[SEAL]

Attest:

SIDNEY A. DIAMOND

Attesting Officer

Commissioner of Patents and Trademarks